United States Patent
Zheng et al.

(10) Patent No.: US 7,998,231 B2
(45) Date of Patent: Aug. 16, 2011

(54) AIR PURIFIER

(75) Inventors: Zhiming Zheng, Sakai (JP); Yasuhiro Oda, Sakai (JP); Tooru Fujimoto, Sakai (JP)

(73) Assignee: Daikin Industries, Ltd., Osaka (JP)

( * ) Notice: Subject to any disclaimer, the term of this patent is extended or adjusted under 35 U.S.C. 154(b) by 229 days.

(21) Appl. No.: 12/445,987

(22) PCT Filed: Dec. 11, 2007

(86) PCT No.: PCT/JP2007/073821
§ 371 (c)(1),
(2), (4) Date: Apr. 17, 2009

(87) PCT Pub. No.: WO2008/072609
PCT Pub. Date: Jun. 19, 2008

(65) Prior Publication Data
US 2010/0293907 A1    Nov. 25, 2010

(30) Foreign Application Priority Data

Dec. 12, 2006    (JP) .................................. 2006-334708

(51) Int. Cl.
*B01D 50/00*    (2006.01)
(52) U.S. Cl. ................ 55/337; 55/467; 55/471; 55/472; 55/473; 55/495; 95/273; 95/268
(58) Field of Classification Search .................... 55/467, 55/471–473, 495, 337; 96/273, 268; 965/273, 965/268
See application file for complete search history.

(56) References Cited

U.S. PATENT DOCUMENTS

| | | | | |
|---|---|---|---|---|
| 2,700,362 A | * | 1/1955 | Calling | 116/271 |
| 2,873,908 A | * | 2/1959 | Powers | 415/211.2 |
| 4,411,675 A | * | 10/1983 | de Castella | 96/140 |
| 4,560,395 A | * | 12/1985 | Davis | 96/381 |
| 4,662,912 A | * | 5/1987 | Perkins | 96/140 |
| 4,894,071 A | * | 1/1990 | Klein | 95/273 |
| 4,990,313 A | * | 2/1991 | Pacosz | 96/224 |

(Continued)

FOREIGN PATENT DOCUMENTS

JP    2002-018219 A    1/2002

(Continued)

OTHER PUBLICATIONS

Daikin Industries, Ltd., "Air Purifier Hikari Criale", product catalog; Aug. 2006; Japan.

(Continued)

*Primary Examiner* — Jason M Greene
*Assistant Examiner* — Dung H Bui
(74) *Attorney, Agent, or Firm* — Global IP Counselors

(57) ABSTRACT

An air purifier includes a housing, a centrifugal fan and an air purifying filter. The fan is substantially centered in the housing. The fan has a rotary shaft extending in a depth direction of the air purifier and a fan inlet port facing frontward. Air suctioned by the fan is blown out in a direction perpendicular to the rotary shaft. The filter is aligned with the fan along the direction perpendicular to the rotary shaft. An air inlet port is disposed in front of the fan so as to communicate with the fan inlet port. When the fan rotates, air is suctioned into the air purifier via the air inlet port. An air outlet port is arranged relative to the filter such that air purified by the filter is blown out of the air purifier through the air outlet port.

16 Claims, 9 Drawing Sheets

U.S. PATENT DOCUMENTS

| | | | | |
|---|---|---|---|---|
| 5,336,285 | A * | 8/1994 | Grandek et al. | 55/324 |
| 5,435,817 | A * | 7/1995 | Davis et al. | 55/337 |
| 5,601,636 | A * | 2/1997 | Glucksman | 96/63 |
| 5,643,079 | A * | 7/1997 | Miyata et al. | 454/134 |
| 5,862,737 | A * | 1/1999 | Chiu et al. | 96/416 |
| 5,984,991 | A * | 11/1999 | Glucksman | 55/471 |
| 6,156,085 | A * | 12/2000 | Chiu et al. | 55/357 |
| 6,156,090 | A | 12/2000 | Ishikawa et al. | |
| 6,168,517 | B1 * | 1/2001 | Cook | 454/269 |
| 6,361,590 | B1 * | 3/2002 | Gilbert et al. | 96/384 |
| 6,494,940 | B1 * | 12/2002 | Hak | 96/224 |
| 6,679,940 | B1 * | 1/2004 | Oda | 96/55 |
| 6,723,159 | B2 * | 4/2004 | Cheng | 96/421 |
| 6,761,859 | B1 * | 7/2004 | Oda | 422/186.3 |
| 6,797,041 | B2 * | 9/2004 | Brownell et al. | 95/268 |
| 6,913,637 | B2 * | 7/2005 | Kim | 95/8 |
| 7,025,798 | B2 * | 4/2006 | Endo | 55/385.1 |
| 7,083,659 | B1 * | 8/2006 | Joyce et al. | 55/385.1 |
| 7,112,232 | B2 * | 9/2006 | Chang et al. | 55/481 |
| 7,163,567 | B2 * | 1/2007 | Choi | 55/312 |
| 7,316,732 | B2 * | 1/2008 | Taylor et al. | 95/141 |
| 7,419,533 | B2 * | 9/2008 | Son et al. | 96/55 |
| 7,585,344 | B2 * | 9/2009 | Paterson et al. | 55/413 |
| 7,632,340 | B2 * | 12/2009 | Brady et al. | 96/26 |
| 7,691,164 | B2 * | 4/2010 | Kellermann | 55/467 |
| 7,708,792 | B2 * | 5/2010 | Kowalski | 55/385.3 |
| 7,857,884 | B2 * | 12/2010 | Bohlen | 55/471 |
| 2001/0049927 | A1 * | 12/2001 | Toepel | 55/385.2 |
| 2003/0150326 | A1 * | 8/2003 | Chasen | 95/273 |
| 2004/0025697 | A1 * | 2/2004 | Endo | 96/222 |
| 2004/0118093 | A1 * | 6/2004 | Chang et al. | 55/471 |
| 2004/0144249 | A1 * | 7/2004 | Kang et al. | 95/1 |
| 2004/0244403 | A1 | 12/2004 | Kim et al. | |
| 2005/0268583 | A1 * | 12/2005 | Han et al. | 55/471 |
| 2006/0185333 | A1 * | 8/2006 | Huehn et al. | 55/471 |
| 2006/0201119 | A1 * | 9/2006 | Song | 55/471 |
| 2006/0217056 | A1 * | 9/2006 | Gomi et al. | 454/187 |
| 2007/0066215 | A1 * | 3/2007 | Song et al. | 454/329 |
| 2007/0113527 | A1 * | 5/2007 | Song et al. | 55/471 |
| 2007/0137489 | A1 * | 6/2007 | Luo | 96/224 |
| 2007/0221061 | A1 * | 9/2007 | Steiner et al. | 96/63 |
| 2008/0000205 | A1 * | 1/2008 | Bohlen | 55/471 |
| 2010/0186357 | A1 * | 7/2010 | Takeda et al. | 55/471 |

FOREIGN PATENT DOCUMENTS

| | | |
|---|---|---|
| JP | 2003-106581 A | 4/2003 |
| JP | 2005-274004 A | 10/2005 |
| WO | WO-98/38458 A1 | 9/1998 |
| WO | WO-01/10537 A1 | 2/2001 |

OTHER PUBLICATIONS

European Search Report of corresponding European Application No. 07 85 0387.7 dated May 31, 2010.

* cited by examiner

AIR PURIFIER

CROSS-REFERENCE TO RELATED APPLICATIONS

This U.S. National stage application claims priority under 35 U.S.C. §119(a) to Japanese Patent Application Nos. 2006-334708, filed in Japan on Dec. 12, 2006, the entire contents of which are hereby incorporated herein by reference.

TECHNICAL FIELD

The present invention relates to an air purifier, and more particularly to an air purifier that can be reduced in its thickness.

BACKGROUND ART

For example, Japanese Laid-Open Patent Publication No. 2003-106581 and product catalog "DAIKIN air purifier, HIKARI CRIALE", DAIKIN INDUSTRIES, Ltd., August, 2006 disclose conventional typical air purifiers. In the conventional air purifiers, an air purifying filter having an electrostatic dust collecting filter portion and a deodorizing filter portion is provided in front of a motor driving fan that has a rotary shaft extending in the depth direction of the air purifier, that is, in a front-and-rear direction. This increases the size of the conventional air purifier in its depth direction. Therefore, when being used in a room, the conventional air purifier occupies undesirably large space.

SUMMARY OF THE INVENTION

Accordingly, an objective of the present invention is to provide an air purifier that is small in its thickness.

To achieve the above objective, the present invention provides an air purifier. The air purifier has a housing (casing) with a centrifugal fan is arranged at a substantially center in the housing. The centrifugal fan has a rotary shaft extending in a depth direction of the air purifier and a fan inlet port that faces frontward in the air purifier. Air that is suctioned by the centrifugal fan via the fan inlet port is blown out from the centrifugal fan in a direction perpendicular to the rotary shaft of the centrifugal fan. An air purifying filter is aligned with the centrifugal fan along the direction perpendicular to the rotary shaft of the centrifugal fan. An air inlet port is provided forward of the centrifugal fan so as to communicate with the fan inlet port of the centrifugal fan. Air is suctioned to the inside of the air purifier via the air inlet port by rotation of the centrifugal fan. An air outlet port is provided corresponding to the air purifying filter so as to blow out the air purified by the air purifying filter to the outside of the air purifier.

DETAILED DESCRIPTION OF THE INVENTION

One embodiment of the present invention will be explained with reference to FIGS. 1 to 5.

Figure 1:
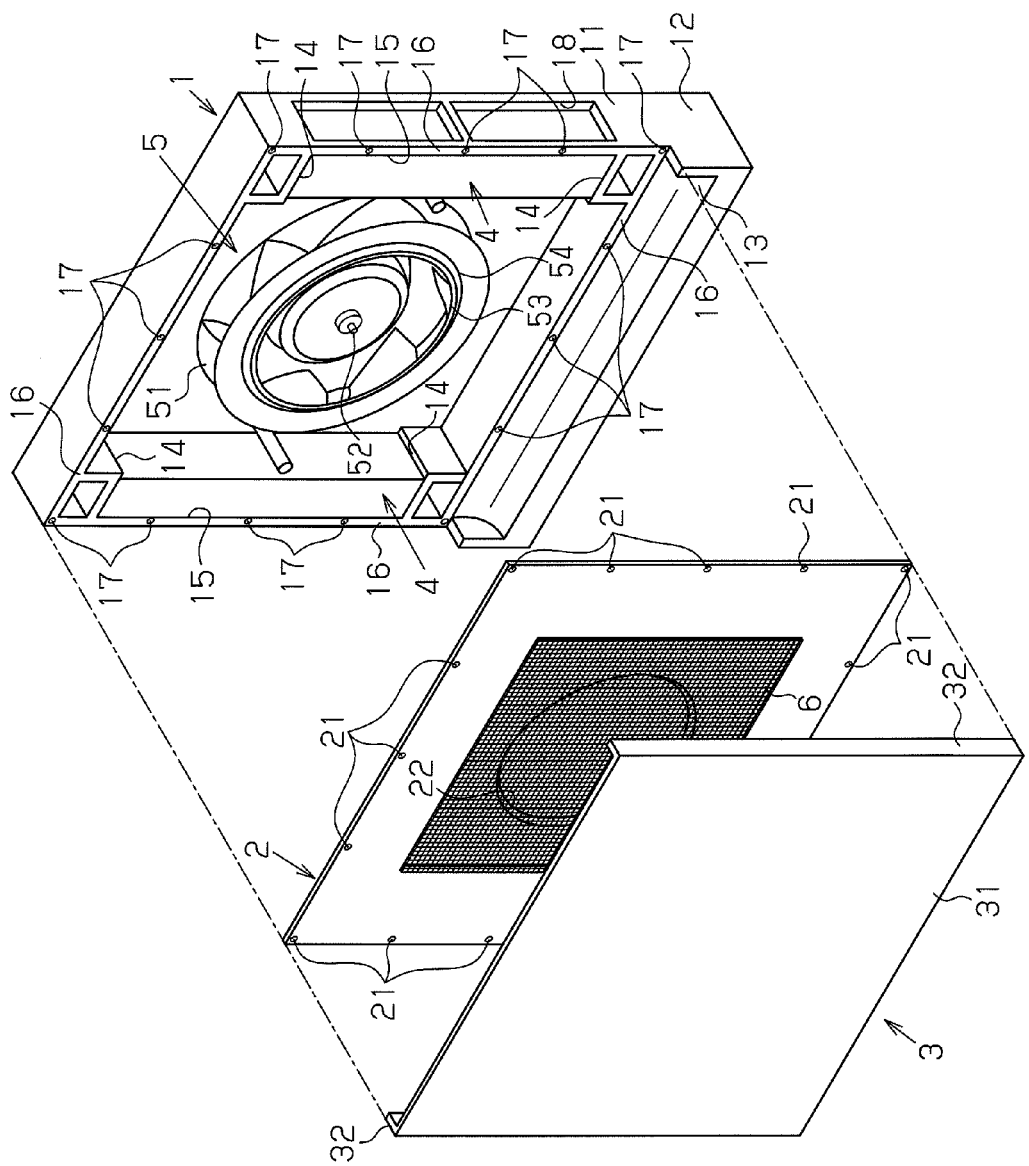
FIG. 1 is an exploded perspective view of an air purifier according to one embodiment of the present invention.

An air purifier according to the present embodiment is a floor model. As shown in FIG. 1, the casing (housing) of the air purifier includes a body casing 1 that is formed in a box and open frontward, a partition plate 2 that is provided on the front side of the body casing 1, and a front panel 3 that is provided on the front surface of the partition plate 2.

Figure 4:
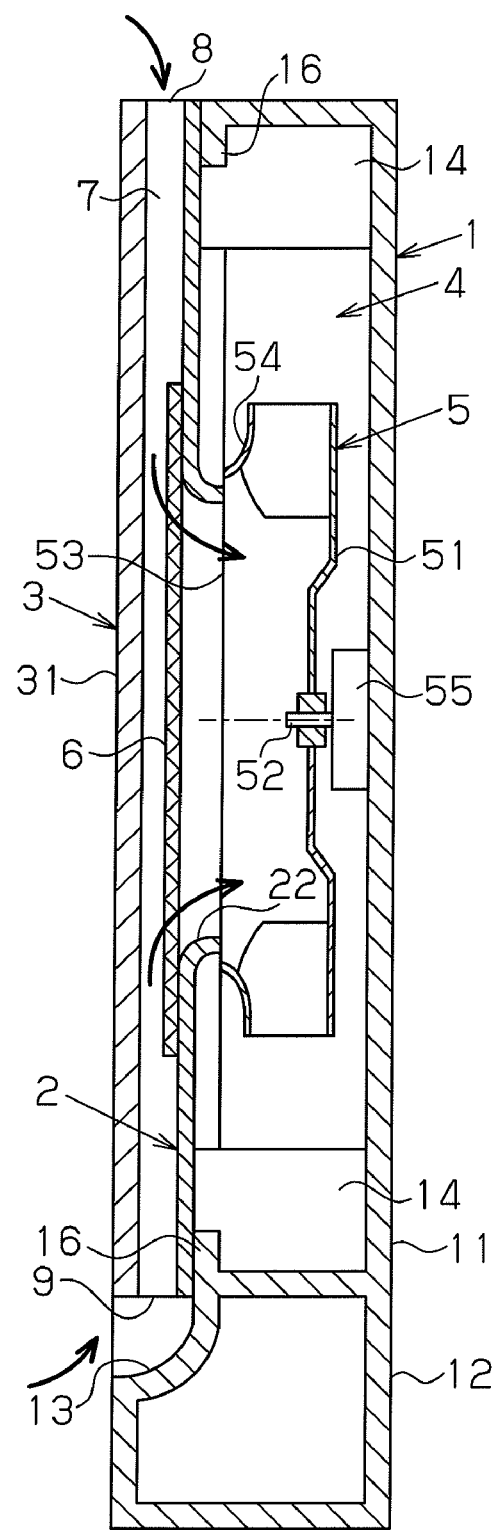
FIG. 4 is a cross-sectional side view of the air purifier shown in FIG. 1.

A portion from the upper portion to the middle portion of the body casing 1 forms a thin portion 11 that is thinner than the lower portion of the body casing 1. The lower portion of the body casing 1, which is thicker than the thin portion 11, forms an electric component accommodation portion 12. The electric component accommodation portion 12 functions as a base member of the air purifier. As shown in FIG. 4, a recess 13 is formed on the front upper side of the electric component accommodation portion 12. The recess 13 is defined by a curved surface that extends continuously from the front surface of the thin portion 11. The recess 13 is connected to a lower air inlet port 9 that is formed between the lower ends of the partition plate 2 and the front panel 3. The lower front surface of the electric component accommodation portion 12 is flush with the front surface of the front panel 3. The partition plate 2 and the front panel 3 are provided at the front side of the thin portion 11.

As shown in FIG. 1, a step portion 14 is formed at each of four corners of the thin portion 11. An air purifying filter 4 is accommodated in a space 15 formed between each upper step portion 14 and the corresponding lower step portion 14. An inward flange 16 is formed at the periphery of the front surface of the thin portion 11. A plurality of threaded holes 17 are formed on the inward flange 16 so as to be used when the partition plate 2 is mounted to the body casing 1.

The air purifying filters 4, which are provided on the left side and the right side in the body casing 1, remove contaminant in air such as floating contamination particles or gaseous pollutant to purify the air. The air purifying filters 4 are simplified in the drawings and may be those that have been known. For example, each air purifying filter 4 has a bio-antibody filter portion, an electrostatic dust collecting filter portion, and a deodorization filter portion. The bio-antibody filter portion adsorbs and removes virus floating in the air by bio-antibody. The electrostatic dust collecting filter portion has a plasma ionization portion that charges dust and pollen in the air to be positive and a filter that is charged to be negative to adsorb and remove the dust and pollen that is charged to be positive. The electrostatic dust collecting filter portion is preferably arranged at the downstream of the bio-antibody filter. A photocatalyst titanium apatite filter may be used for the deodorization filter portion that decomposes an odor component in the air. The photocatalyst titanium apatite filter has an ability to adsorb mold or virus. The deodorization filter portion is preferably arranged at the downstream of the electrostatic dust collecting filter.

Figure 3:
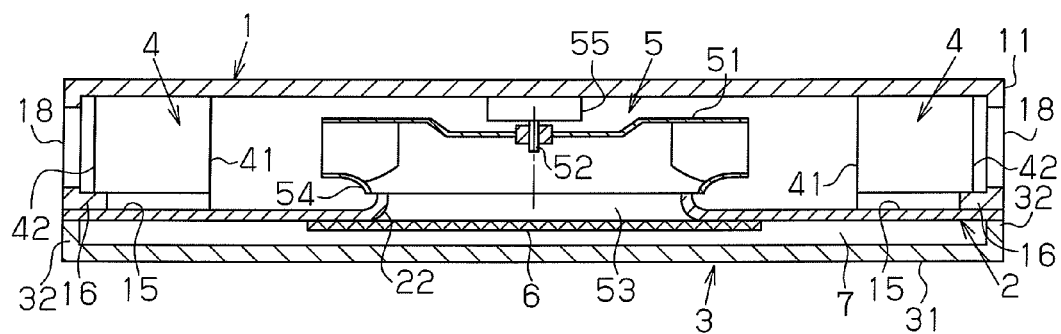
FIG. 3 is a cross-sectional plan view of the air purifier shown in FIG. 1.

The air purifying filters 4 have the same shape and size as each other. Specifically, each air purifying filter 4 has an outer shape of a rectangular parallelepiped that matches with the space 15 that accommodates the air purifying filter 4. As shown in FIG. 3, each air purifying filter 4 has an air inlet side 41 and an air outlet side 42 that are arranged to opposite to each other. The air purifying filters 4 are arranged such that air inlet sides 41 and the air outlet sides 42 are perpendicular to the front surface of the thin portion 11. When the front panel 3 and the partition plate 2 are detached from the body casing 1, the air purifying filters 4 can be removed forward (from the front side of the air purifier).

Air outlet ports 18 are formed on each of the left and right sides of the body casing 1 so as to face the air outlet side 42 of the corresponding air purifying filter 4. The air that is purified by each air purifying filter 4 is blown out of the air purifier through the corresponding air outlet ports 18.

A centrifugal fan 5 is arranged at the center in the body casing 1. The centrifugal fan 5 may be a turbofan. The centrifugal fan 5 has an impeller 51 and a rotary shaft 52 extending in the depth direction of the air purifier, that is, a front-and-rear direction. An inlet port 53 of the centrifugal fan 5 that is defined by a shroud 54 faces frontward (at the front side of the air purifier). A fan motor 55 that activates the centrifugal fan is attached to a rear plate of the body casing 1. The air that is suctioned to the centrifugal fan 5 through the inlet port 53 is blown out from the centrifugal fan 5 by the rotating impeller 51 to the radial direction of the centrifugal fan 5, that is, a direction perpendicular to the rotary shaft 52 of the centrifugal fan 5. That is, the air purifying filters 4 are arranged to be aligned with the centrifugal fan 5 along a direction perpendicular to the rotary shaft 52 of the centrifugal fan 5. Therefore, the air purifying filters 4 are arranged at the outlet side of the centrifugal fan 5.

As shown in FIG. 1, the partition plate 2 is flat and through holes 21 are formed at the periphery of the partition plate 2 so as to correspond to threaded holes 17 that are formed on the inward flange 16 of the body casing 1. A screw (not shown) is passed through each through hole 21 to be screwed to the corresponding threaded hole 17. Accordingly, the partition plate 2 is attached to the body casing 1. A bellmouth 22 is formed at the center of the partition plate 2, corresponding to the shroud 54 (inlet port 53) of the centrifugal fan 5. A pre-filter 6 is attached to the front surface of the partition plate 2 so as to cover the bellmouth 22. The pre-filter 6 is, for example, a catechin-containing filter, and not only collects large dust or hair of pets but also has a sterilizing effect against bacteria or mold that is adhered to the collected dust. The partition plate 2 partially defines the spaces 15 that accommodate the air purifying filters 4. The partition plate 2 also defines the boundary between the inlet side and the outlet side of the centrifugal fan, that is, between a front area and a rear area of the centrifugal fan 5.

The front panel 3 has a plate portion 31 having a flat front surface and bent portions 32 which are bent from the left side and the right side of the plate portion 31 to extend rearward. The front panel 3 is detachably attached to the body casing 1 or the partition plate 2 in an appropriate method such that the distal end of each bent portion 32 is brought into contact with the front surface of the partition plate 2. Therefore, a space 7 is formed between the partition plate 2 and the front panel 3 and has a size corresponding to the size of the bent portions 32. The space 7 communicates with the outside of the air purifier via an upper air inlet port 8 formed as a slit between the upper ends of the front panel 3 and the partition plate 2, and a lower air inlet port 9 formed as a slit between the lower ends of the front panel 3 and the partition plate 2.

Next, an operation of the air purifier according to the present embodiment will be explained.

When an operation switch (not shown) is turned on, the fan motor 55 is activated to start to rotate the centrifugal fan 5 and start the operation of the air purifying filters 4 having the electrostatic dust collecting filter portion and other filter portions that require electric power. When the centrifugal fan 5 is rotated, air in a room is suctioned to the inside of the air purifier through the air inlet port 8, formed between the upper ends of the front panel 3 and the partition plate 2, as well as through the recess 13, formed on the front surface of the electric component accommodation portion 12, and the air inlet port 9, formed between the lower ends of the front panel 3 and the partition plate 2.

The air thus suctioned through the air inlet ports 8, 9 passes through the space 7 between the front panel 3 and the partition plate 2, the pre-filter 6, and the bellmouth 22 sequentially. After that, the air is suctioned from the inlet port 53 to the centrifugal fan 5 and then blown from the centrifugal fan 5 along the radial direction of the centrifugal fan 5 by the rotating impeller 51. In the process passing through the pre-filter 6, the large dust or hair of pets in the air is collected by the pre-filter 6 and micro-organism such as bacteria and mold adhered to the collected dust is sterilized by catechin in the pre-filter 6.

Figure 2:
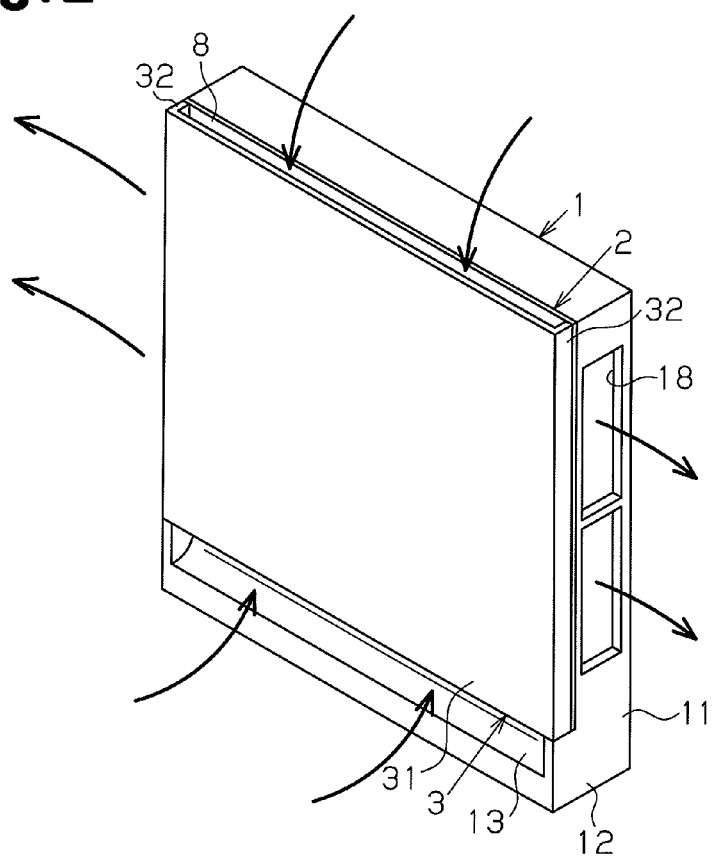
FIG. 2 is a perspective view of the air purifier shown in FIG. 1.

The air blown out from the centrifugal fan 5 in the radial direction passes through the left and right air purifying filters 4. In the process passing through the air purifying filters 4, the floating virus in the air is adsorbed to the bio-antibody filter portions and the dust or pollen in the air is adsorbed to the electrostatic dust collecting filter portions. Further, at the deodorization filter portion of each air purifying filter 4, the odor component in the air is decomposed and bacteria or mold in the air is adsorbed and removed. The purified air passing through the air purifying filters 4 is blown out to the outside of the air purifier from the left and right air outlet ports 18. Arrows of thick solid lines in FIGS. 2 and 4 show the flow of the air.

Figure 5:
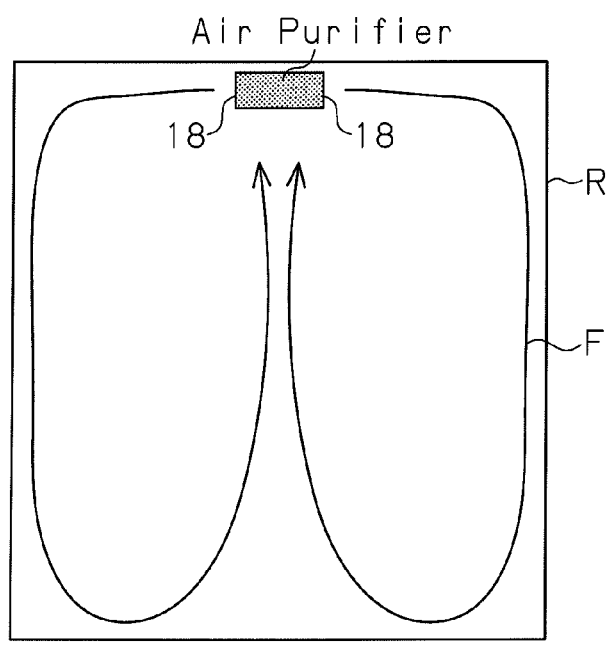
FIG. 5 is a schematic plan view showing the interior of a room where the air purifier shown in FIG. 1 is arranged for explaining air flows in the room caused by the air purifier.

As shown in FIG. 5, it is assumed that the air purifier is arranged at the center of one wall in a room R. The air purifier suctions air in the room from the front side and blows out the purified air from the left and right air outlet ports 18. Therefore, air circulation is generated as shown by arrows F in FIG. 5 such that the air flows from the periphery along the wall surfaces in the room R toward the front surface of the air purifier. As a result, the air in the entire room is purified efficiently.

According to the present embodiment, following advantages are obtained.

The air purifying filters 4 are provided at the left and right sides of the centrifugal fan 5. That is, the air purifying filters 4 and the centrifugal fan 5 are not aligned along the depth direction of the air purifier. Therefore, the depth size of the body casing 1 is reduced and a thinner air purifier is provided. Since the air purifying filters 4 are arranged at the outlet side of the centrifugal fan 5, noise of the air purifier is reduced due to a noise adsorption effect and a noise insulation effect of the air purifying filters 4.

The front surface of the front panel 3 is flat. This improves the appearance of the air purifier and makes cleaning and maintenance of the front panel 3 easy. In the case of the present embodiment, each of the air inlet ports 8, 9 that suction the room air to the inside of the air purifier is formed in a space between the upper ends of the front panel 3 and the partition plate 2 and a space between the lower ends of the front panel 3 and the partition plate 2, respectively. This makes the front surface of the front panel 3 flat.

Each air purifying filter 4 is arranged at the left side or the right side in the body casing 1. That is, the air purifying filters 4 are arranged at a plurality of positions in the body casing 1. This is effective for improving the air purifying efficiency of the air purifier.

The left and right air purifying filters 4 have the same shape and size as each other. Therefore, the wind speed distributions of the filters 4 are easily matched with each other. This is effective for improving the air purifying efficiency of the air purifier.

Each of the air inlet ports 8, 9 that suction the room air to the inside of the air purifier is formed in the space between the upper ends and the lower ends of the front panel 3 and the partition plate 2, respectively, and the air outlet ports 18 that blow out the air purified by the air purifying filters 4 to the outside of the air purifier are formed at the left and right sides of the body casing 1 of the air purifier. Accordingly, the purified air is blown out symmetrically from the left side and the right side with avoiding a short circuit between the air inlet ports 8, 9 and the air outlet ports 18. This configuration also makes the wind speed distributions of the left and right air purifying filters 4 to be matched with each other easily.

As shown in FIG. 5, when the air purifier is arranged at the center of the wall in the room R, the air circulation is generated as shown by arrows F in FIG. 5 such that the air flows from the periphery along the wall surfaces in the room R toward the front surface of the air purifier. Accordingly, the air in the entire room is purified effectively.

The front panel 3 and the partition plate 2 are detached from the body casing 1 such that the air purifying filters 4 are exchanged easily and the cleaning and maintenance of the centrifugal fan 5 are carried out easily.

Since each of the air purifying filters 4 has various functions of collecting dust and deodorization, the air purifier is useful for various usages.

The room air suctioned to the air purifier passes through the pre-filter 6 to the centrifugal fan 5. This prevents relatively large objects such as lint from being suctioned to the centrifugal fan 5. The air suctioned to the centrifugal fan 5 is straitened by the pre-filter 6. This reduces suction resistance of the centrifugal fan 5 and also reduces noise of the centrifugal fan 5.

When a turbofan is used as the centrifugal fan, the running efficiency of the air purifier is increased and thus the energy consumption is reduced.

The above embodiment may be modified as follows.

Modification 1

In the above embodiment, each air purifying filter 4 has the electrostatic dust collecting filter portion and the deodorizing filter portion. However, any one of the filter portions may be omitted. Alternatively, each air purifying filter 4 may have another dust collecting filter portion made of, for example, a HEPA (high efficiency particulate air) filter instead of the electrostatic dust collecting filter portion.

Modification 2

Figure 6:
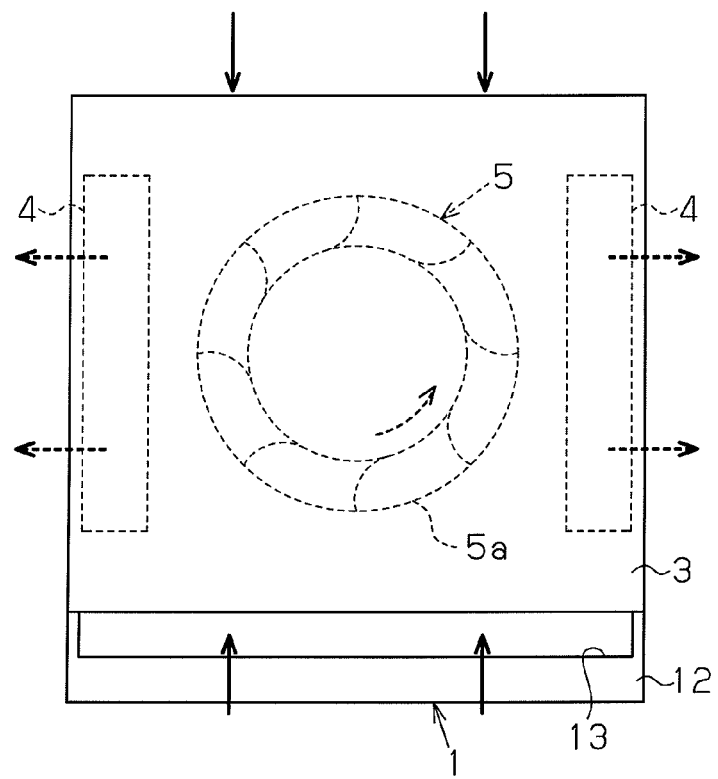
FIG. 6 is a front view of an air purifier according to another embodiment of the present invention.

The centrifugal fan 5 may be comprised of a radial fan 5a shown in FIG. 6 instead of the turbofan. When the radial fan 5a is used as the centrifugal fan 5, the circumferential component is reduced in the blown air flow from the centrifugal fan 5. This reduces the possibility that the suctioned air flow to the centrifugal fan 5 is disturbed by the blown air flow from the centrifugal fan 5. This reduces the suction resistance of the centrifugal fan 5 and the noise of the centrifugal fan 5.

Modification 3

The air purifier of the above embodiment is a floor model. However, the air purifier may be a wall hanging model or a ceiling hanging model. In these cases, the thickness of the electric component accommodation portion 12 may be set to be the same as the thickness of the thin portion 11 such that room air is directly suctioned to the inside of the air purifier from the air inlet port 9 between the lower ends of the front panel 3 and the partition plate 2 without passing through the recess 13. Alternatively, the electric component accommodation portion 12 may be arranged in another position in the body casing 1. In case of the wall having model or the ceiling hanging model, the air purifier is thin similarly to the case of the floor model. Therefore, a user hardly feels pressure when the air purifier is placed in a room.

Modification 4

Figure 7:
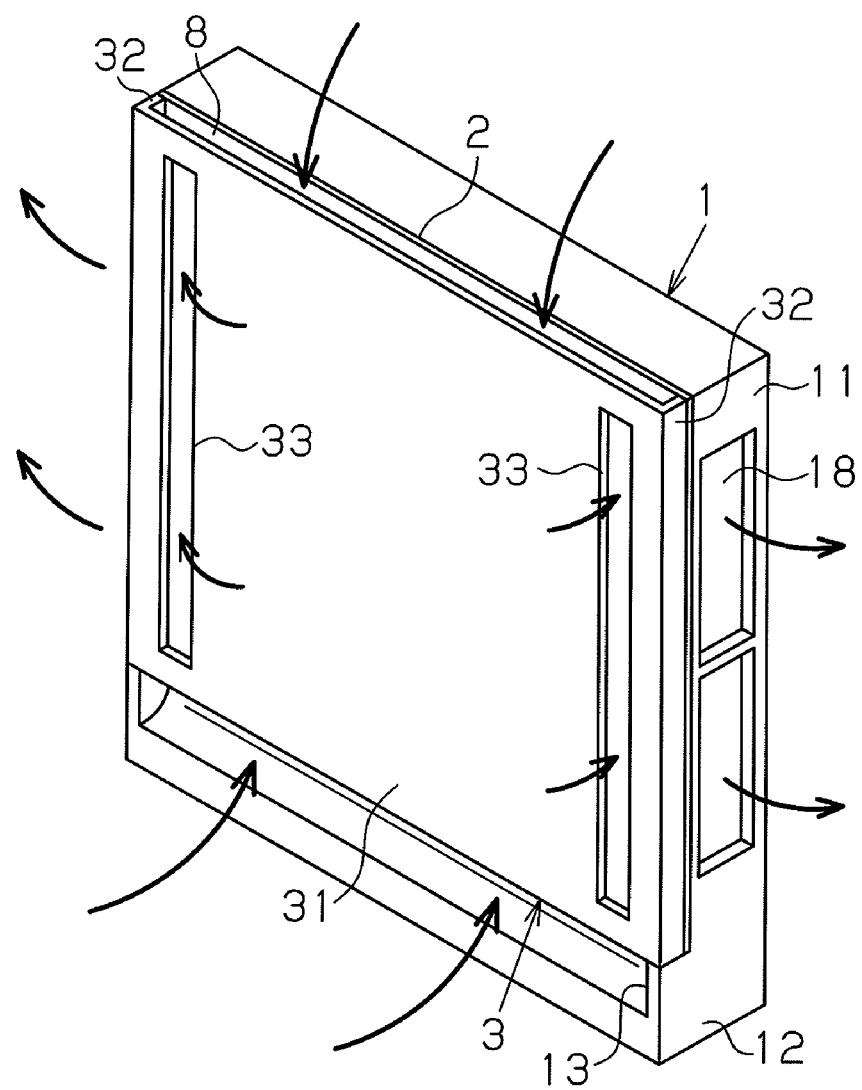
FIG. 7 is a perspective view of an air purifier according to another embodiment of the present invention.

As shown in FIG. 7, a vertically elongated slit 33 may be provided at each of the left and right sides of the front panel 3. The vertically elongated slits 33 each function as an auxiliary air intake port for suctioning room air to the inside of the air purifier. In this case, the suction resistance of the centrifugal fan 5 is reduced. This is effective in reducing energy consumption of the air purifier.

Modification 5

In the above embodiment, the air purifying filters 4 are arranged at the right side and the left side in the body casing 1, and the air purified by the air purifying filters 4 is blown out to the outside of the air purifier via the air outlet ports 18 each of which is provided on the left side or the right side of the body casing 1. This configuration is preferable in a case where the air purifier is hooked on the wall without providing a space between the air purifier and the ceiling when the air purifier is arranged at a center of the wall in the room.

However, when the air purifier is placed on a floor at the corner of the room such that the left or right air outlet ports 18 faces the wall, there is a possibility that the air may not be circulated smoothly in the room. Therefore, for preparation of such use, the air purifying filter 4 may be capable of being arranged at an upper portion in the body casing 1 in addition to the left side and the right side in the body casing 1. Accordingly, a user may select freely the arrangement position of the air purifying filters.

In this case, the air outlet ports 18 are provided on the upper side of the body casing 1 in addition to the left side and the right side. However, it is preferable to prepare a cover for covering the air outlet ports 18 corresponding to the arrangement position of the air purifying filter 4 in the body casing 1 where the air purifying filter 4 is not arranged.

When the air outlet ports 18 are provided on the upper side of the body casing 1, it is preferable to form on the front panel 3 a bent portion that extends from the upper edge of the plate portion 31 to the rear side to cover the upper air inlet port 8 in order to prevent a short circuit between the upper air outlet ports 18 and the upper air inlet port 8. When the upper air inlet port 8 is covered, the elongated slit similar to the elongated slit 33 shown in FIG. 7 is preferably formed at each of the left and right sides of the front panel 3.

Figure 8A:
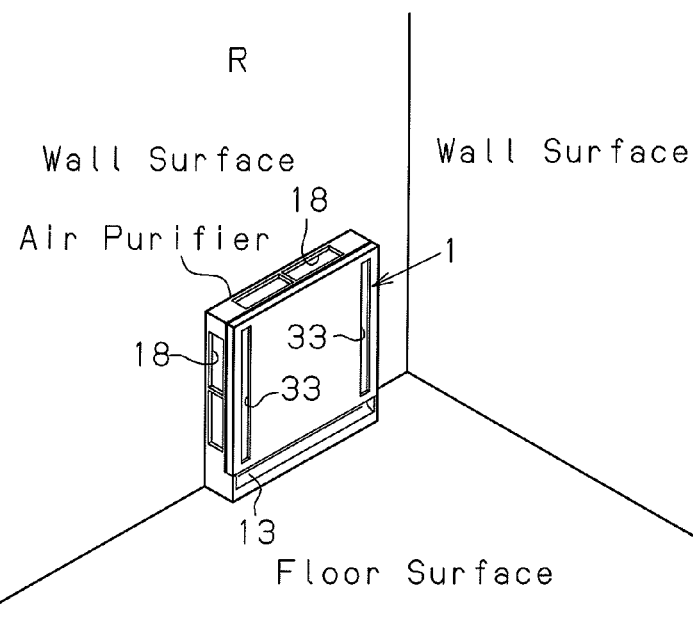
FIG. 8(a) is a perspective view of an air purifier according to another embodiment of the present invention that is arranged in a room.
Figure 8B:
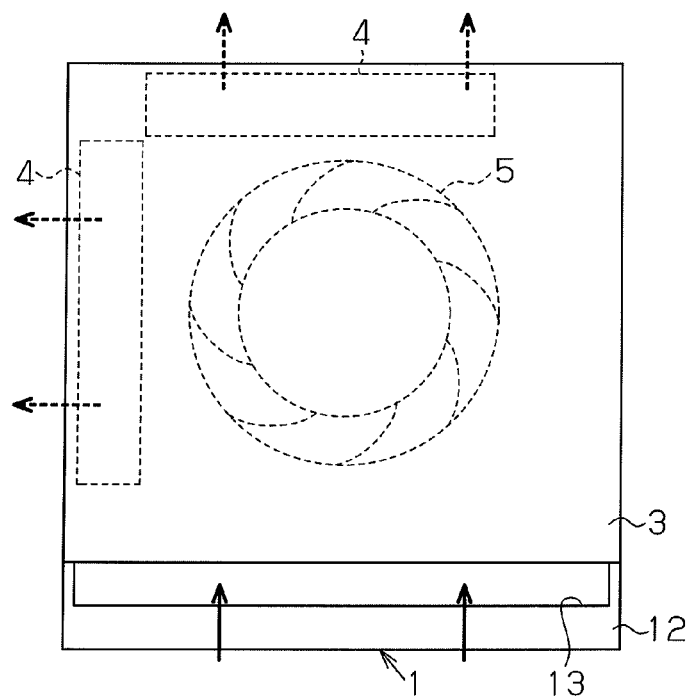
FIG. 8(b) is a front view of the air purifier shown in FIG. 8(a)

In case of applying the above configuration, for example, when the air purifier is placed on a floor at a corner of the room R such that the right air outlet ports 18 face the wall as shown in FIG. 8(a), the right air outlet ports 18 are covered with a cover. The air purifying filters 4 are arranged at the left side and the upper side in the body casing 1 as shown in FIG. 8(b).

Figure 9A:
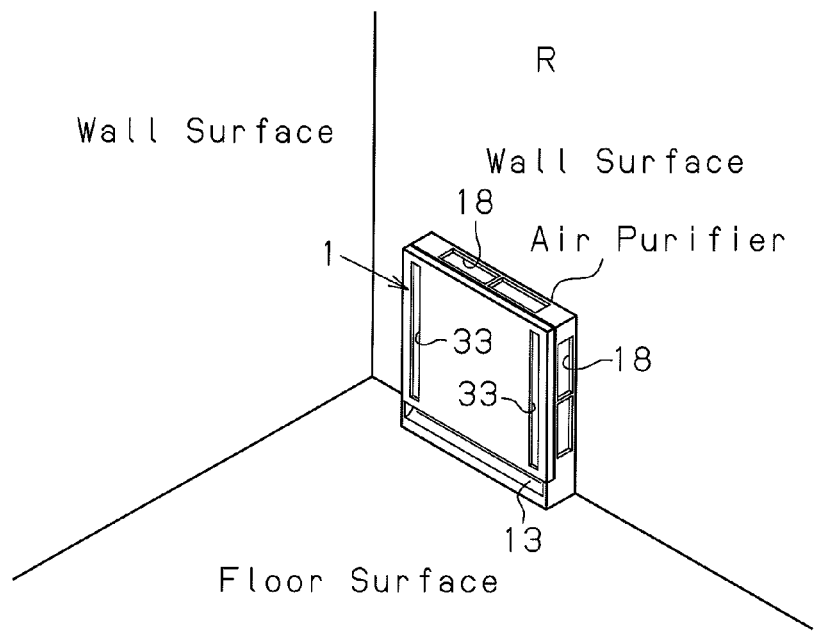
FIG. 9(a) is a perspective view of an air purifier according to another embodiment of the present invention that is arranged in a room.
Figure 9B:
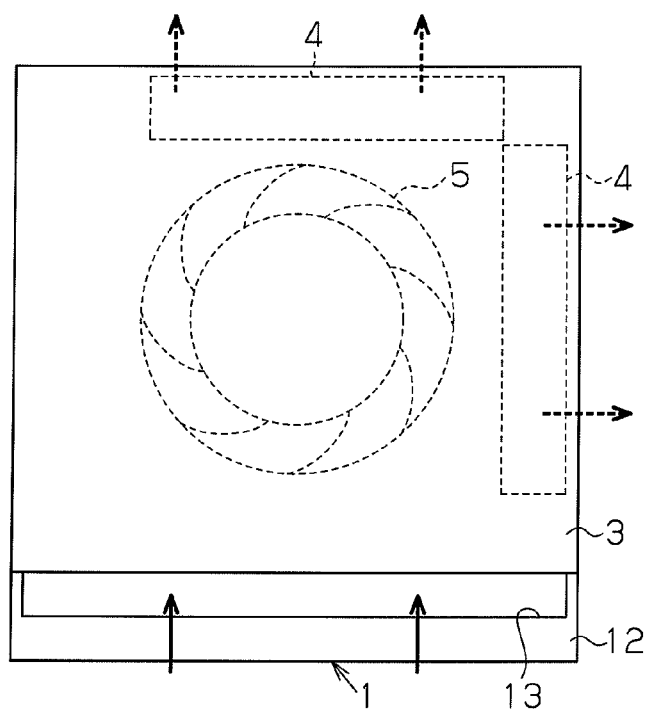
FIG. 9(b) is a front view of the air purifier shown in FIG. 9(a)

On the other hand, when the air purifier is placed on a floor at a corner of the room R such that the left air outlet ports 18 face the wall as shown in FIG. 9(a), the left air outlet ports 18 are covered with a cover. The air purifying filters 4 are arranged at the right side and the upper side in the body casing 1 as shown in FIG. 9(b). Accordingly, the air in the room is circulated in a favorable manner.

Modification 6

Figure 10:
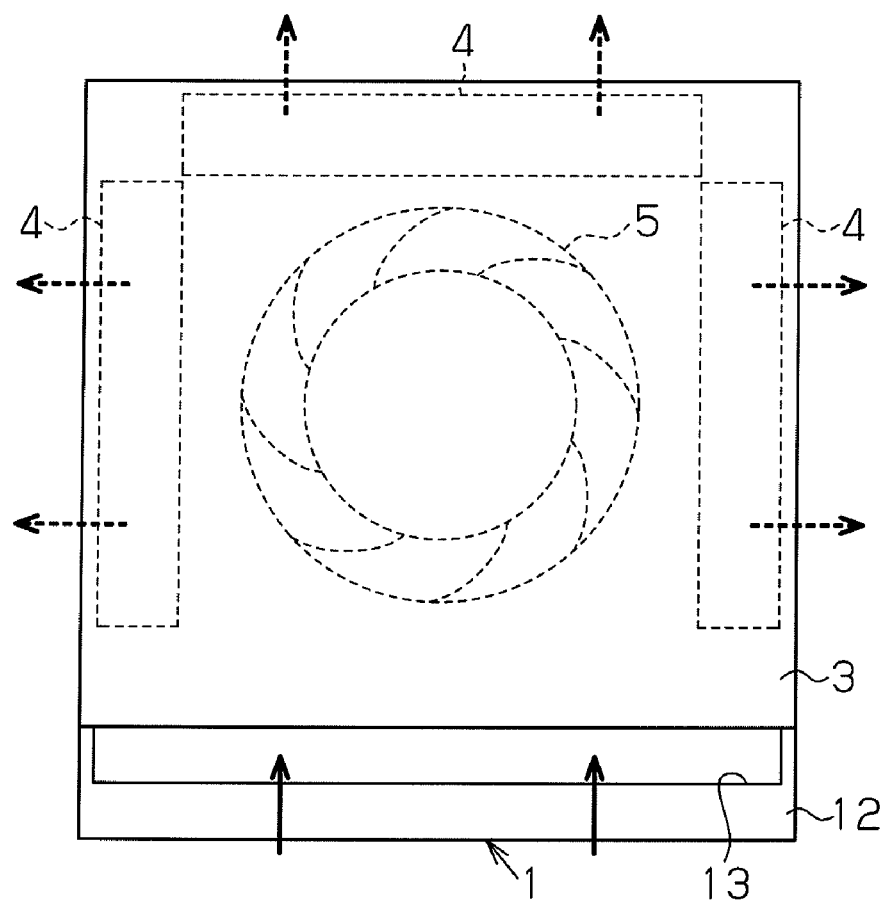
FIG. 10 is a plan view of an air purifier according to another embodiment of the present invention.

When the air purifier is placed on a floor at the center of the wall in the room, the air purifying filter 4 may be arranged on the upper side in the body casing 1 in addition to the left side and the right side as shown in FIG. 10. In this case, the air outlet ports 18 is provided on the upper side of the body casing 1 in addition to the left and right sides. A bent portion extending from the upper edge of the plate portion 31 to the rear side may be formed on the front panel 3 to cover the upper air inlet port 8 in order to prevent a short circuit between the upper air outlet ports 18 and the upper air inlet port 8. Further, an elongated slit similar to the elongated slits 33 shown in FIG. 7 is formed on each of the left and right sides of the front panel 3. This improves the air purifying efficiency of the air purifier.

Modification 7

Figure 11:
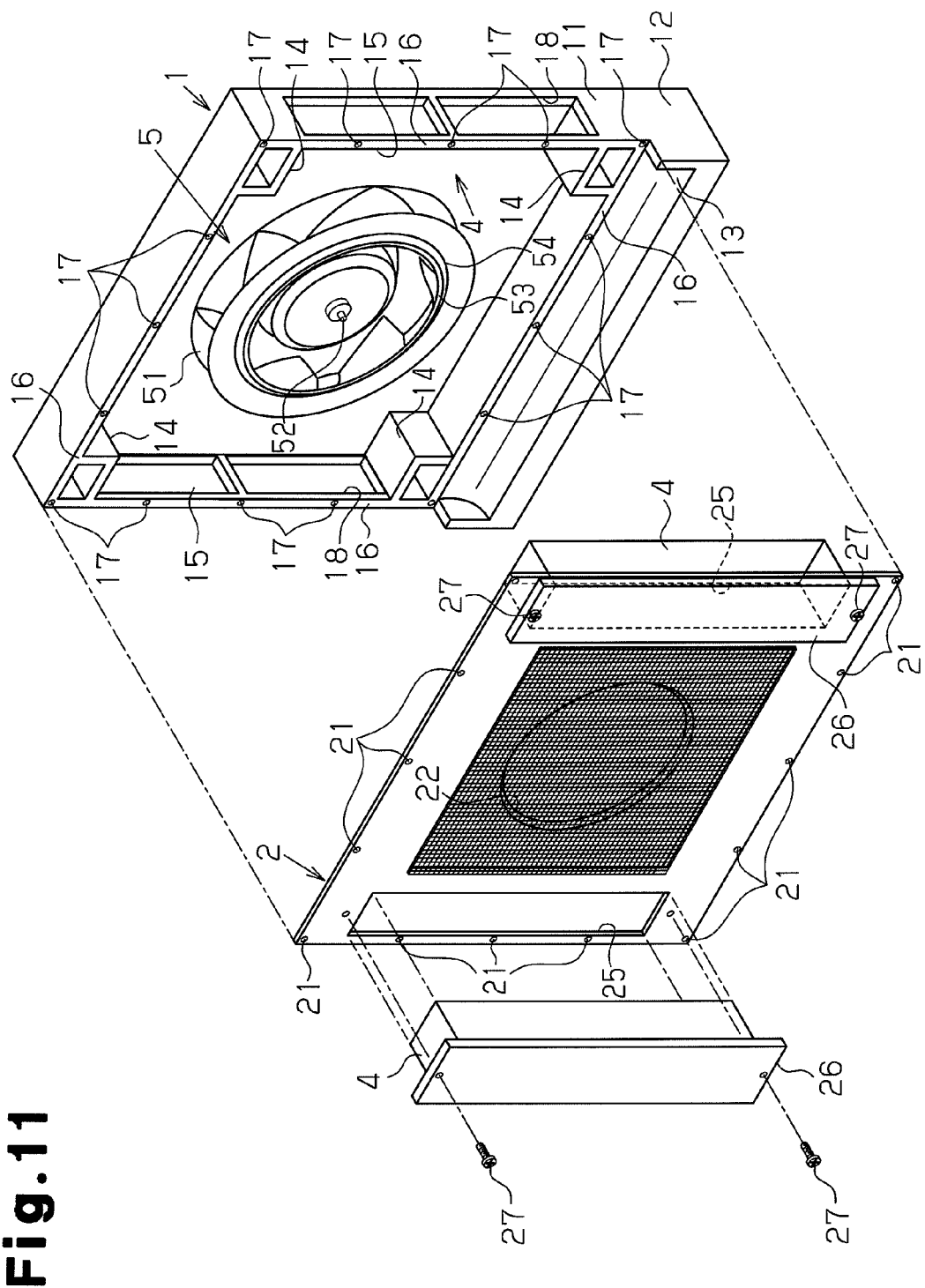
FIG. 11 is an exploded perspective view of an air purifier according to another embodiment of the present invention.

In the above embodiment, the air purifying filters 4 can be attached to and detached from the body casing 1 in a state where the front panel 3 and the partition plate 2 are removed from the body casing 1. However, it may be configured that the air purifying filters 4 can be attached to and detached from the body casing 1 in a state where at least the partition plate 2 is attached to the body casing 1. Specifically, as shown in FIG. 11, service openings 23 for receiving the air purifying filters 4 are formed on the left and right sides of the partition plate 2. Each service opening 23 is closed by attaching a service cover 26 with screws 27 at portions of the partition plate 2 around the service opening 23. The screw is inserted from the front side to the rear side of the partition plate 2. The air purifying filter is detachably attached to the rear side of each service cover 26.

What is claimed is:

1. An air purifier comprising:
   a housing having an air inlet port and an air outlet port;
   a centrifugal fan substantially centered in the housing, the centrifugal fan having a rotary shaft extending in a depth direction of the air purifier and a fan inlet port that faces frontward in the air purifier such that suctioned by the centrifugal fan via the fan inlet port is blown out from the centrifugal fan in a direction perpendicular to the rotary shaft of the centrifugal fan; and
   an air purifying filter aligned with the centrifugal fan along the direction perpendicular to the rotary shaft of the centrifugal fan,
   the air inlet port of the housing being disposed in front of the centrifugal fan so as to communicate with the fan inlet port of the centrifugal fan such that air is suctioned into the air purifier via the air inlet port by rotation of the centrifugal fan, and
   the air outlet port of the housing being arranged relative to the air purifying filter such that air purified by the air purifying filter is blown out of the air purifier through the air outlet port,
   the air purifying filter including parts each arranged in one of at least two portions selected from a left portion, a right portion, and an upper portion in the housing, and
   the air outlet port includes parts each disposed on one of at least two of a left side, a right side, and an upper side of the housing corresponding to the at least two portions in the housing where the air purifying filter is arranged.

2. The air purifier according to claim 1, wherein
   each of the left portion, the right portion, and the upper portion in the housing is configured such that one of the air purifying filter parts can be arranged therein, and
   the air purifying filter parts are is arranged in two of the portions in the housing.

3. The air purifier according to claim 1, wherein
   each of the air purifying filter parts includes at least one of a dust collecting filter portion and a deodorization filter portion.

4. The air purifier according to claim 1, wherein
   the centrifugal fan is a turbofan.

5. The air purifier according to claim 1, wherein
   the centrifugal fan is a radial fan.

6. The air purifier according to claim 1, wherein
   the air purifying filter parts have substantially the same shape and size as each other.

7. The air purifier according to claim 1, wherein
   the air purifying filter parts are arranged in the left portion, the right portion, and the upper portion in the housing, and
   the air outlet port parts are formed on the left side, the right side, and the upper side of the housing.

8. The air purifier according to claim 7, wherein
   the air purifying filter parts have substantially the same shape and size as each other.

9. The air purifier according to claim 1, wherein
   the housing includes
     a body casing that is substantially box shaped and has an open front,
     a partition plate attached to the open front of the body casing, the partition plate having a bell mouth aligned with the fan inlet port of the centrifugal fan, and
     a front panel attached to a front side of the partition plate to form a predetermined space between the front panel and the partition plate, the space between the front panel and the partition plate communicating with the air inlet port.

10. The air purifier according to claim 9, wherein
    the partition plate is detachable from the body casing, and
    the air purifying filter parts are removable from a front side of the air purifier when the partition plate is detached from the body casing.

11. The air purifier according to claim 9, wherein
    the air inlet port includes a slit formed between corresponding end portions of the front panel and the partition plate.

12. The air purifier according to claim 9, wherein
    the air purifying filter parts are arranged in the left portion and the right portion in the housing,
    the air outlet port parts are formed on the left side and the right side of the housing, and
    the air inlet port includes a slit formed between upper ends of the front panel and the partition plate and a slit formed between lower ends of the front panel and the partition plate.

13. The air purifier according to claim 9, wherein
    the front panel includes an elongated slit formed at a left side thereof and an elongated slit formed at a right side thereof, and
    air is suctioned into the air purifier via the elongated slits and the air inlet port when the centrifugal fan rotates.

14. The air purifier according to claim 9, wherein
    each of the air purifying filter parts has a substantially rectangular parallelepiped outer shape, each of the air purifying filter parts has an air inlet side and an air outlet side that are arranged on opposite sides thereof relative to each other, and the air inlet side and the air outlet side of each air purifying filter part are perpendicular to the open front of the body casing.

15. The air purifier according to claim 9, wherein the partition plate includes a pre-filter is attached to the front side thereof to cover the bell mouth.

16. The air purifier according to claim 9, wherein
the air purifying filter parts are arranged in the left portion, the right portion, and the upper portion in the housing, and
the air outlet port parts are parts formed on the left side, the right side, and the upper side of the housing.

* * * * *